US009909810B2

(12) United States Patent
Broekmans et al.

(10) Patent No.: US 9,909,810 B2
(45) Date of Patent: Mar. 6, 2018

(54) IMMERSION DEVICE FOR MOLTEN METAL AND STEELMAKING METHOD

(71) Applicant: Heraeus Electro-Nite International N.V., Houthalen (BE)

(72) Inventors: Gerrit Broekmans, Paal (BE); Jan Cuypers, Kermt (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 8 days.

(21) Appl. No.: 15/178,163

(22) Filed: Jun. 9, 2016

(65) Prior Publication Data

US 2016/0363374 A1 Dec. 15, 2016

(30) Foreign Application Priority Data

Jun. 11, 2015 (EP) .................................... 15171672

(51) Int. Cl.
| | |
|---|---|
| *F27D 21/00* | (2006.01) |
| *G01N 1/12* | (2006.01) |
| *C21C 5/00* | (2006.01) |
| *G01K 1/12* | (2006.01) |

(52) U.S. Cl.
CPC ............ *F27D 21/0014* (2013.01); *C21C 5/00* (2013.01); *F27D 21/0028* (2013.01); *G01K 1/12* (2013.01); *G01N 1/125* (2013.01); *F27M 2001/02* (2013.01)

(58) Field of Classification Search
CPC ............... C21C 5/00; G01K 1/12; G01K 1/14
USPC ......................................................... 266/79
See application file for complete search history.

(56) References Cited

U.S. PATENT DOCUMENTS

| | | |
|---|---|---|
| 3,791,220 A | 2/1974 | Falk et al. |
| 4,566,343 A | 1/1986 | Theuwis et al. |
| 2016/0363374 A1* | 12/2016 | Broekmans ............... C21C 5/00 |

FOREIGN PATENT DOCUMENTS

| | | |
|---|---|---|
| DE | 10202357 A1 | 1/2003 |
| EP | 0143498 A2 | 6/1985 |
| EP | 0237056 A2 | 9/1987 |
| JP | 2000028438 A | 1/2000 |

OTHER PUBLICATIONS

Extended Search Report dated Dec. 21, 2015 in EP Application No. 15171672.7.

* cited by examiner

*Primary Examiner* — Scott Kastler
(74) *Attorney, Agent, or Firm* — Panitch Schwarze Belisario & Nadel LLP

(57) ABSTRACT

An immersion device is provided for molten metal, as well as a method for making steel. The immersion device allows a trouble free operation. The immersion device includes a measuring head, a carrier for the measuring head, and a lance detachably connected to the carrier, preferably by a detachable tubular connecting element. A gas path runs from the lance to the detachable tubular connecting element. A gas tight connection is provided between a connecting surface of the lance and the detachable tubular connecting element. The tubular connecting element has wipers in the form of fins, which wipe the connecting surface of the lance during attaching and/or detaching the tubular connecting element and the lance.

14 Claims, 1 Drawing Sheet

IMMERSION DEVICE FOR MOLTEN METAL AND STEELMAKING METHOD

BACKGROUND OF THE INVENTION

The invention relates to an immersion device for molten metal, the device comprising a carrier for a measuring head and a lance which is detachably connected to the carrier or can be connected to the carrier by a detachable tubular connecting element and comprising a gas path from the lance to the detachable tubular connecting element and a gas tight connection between a connecting surface of the lance and the detachable tubular connecting element. The invention further relates to a method for making steel.

An immersion device comprising a lance and a carrier is known, for example, from European patent application publication EP 0 143 498 A2. A lance of an immersion device is or can be connected to the carrier by a detachable tubular connecting element or coupling piece as known, for example, from U.S. patent application publication No. 2014/0318276 A1.

The measuring head of the carrier may comprise a sampler for taking samples from melts having a melting point higher than 600° C., in particular for metal or cryolite melts, especially iron or steel melts. The carrier may have an immersion end and a sample chamber assembly arranged on the immersion end of the carrier. The assembly may have an inlet opening and a sample cavity for the melt and can be arranged at least partially inside the carrier.

The measuring head of the carrier may comprise one or more sensors. Sensor output terminals are electrically attached to a contact end of the lance.

The lance serves for the automated machine handling or manual handling of the carrier having the measuring head. Using the lance, the carrier comprising the measuring head is immersed in the metal melt and withdrawn from the melt after obtaining the measurement and/or sample. The carrier having the measuring head is a disposable article, which is disposed of after being used once, while the lance is used multiple times.

Disposable carriers having a measuring head for obtaining measurements and metallurgical samples are described, for example, in U.S. Pat. Nos. 5,515,739 and 8,479,579 B2. These devices typically comprise a measuring head with sensors for detecting one or more of temperature, oxygen content, carbon content, bath level, and a representative sample of the liquid steel, in order to monitor the molten metal and control its processing. The measuring head is supported by the carrier protecting the internal wiring and electrical connections. The carrier is comprised of overlying layers of cardboard tubes. During immersion into molten metal, the outer circumference of cardboard deteriorates quickly but is sufficiently thick to last tens of seconds during which measurements are obtained and a metallurgical metal sample withdrawn from the bath. The measuring head is removed from the lance, the metallurgical sample retrieved and the spent probe is discarded. The DC voltage data of the sensors are automatically fed to a computer which compares the actual bath conditions with a model prediction to suggest further actions to be taken to complete the steelmaking process to the target requirements.

The accuracy of the input data is dependent upon a high quality electrical connection between the output connector of the probe and receiving contacts of the lance. Whereas, for example, a connector of a sensor is used just once and the sensor discarded after each use, the receiving contacts of the lance must be designed to withstand repeated use. When immersed into the molten steel, the cardboard carriers are heated, emitting water vapor, tar and resins present in the cardboard carriers. The water vapor transports these tars and resins which deposit upon the colder metallic portions of the electrical contact and its housing, resulting in interruption and deterioration of the electrical sensor signals and consequently in an unavailability of data or incorrect data. Each successive use of the lance deposits more and more of the tars and resins, and when these harden, they present a barrier to subsequent electrical connection, necessitating a rigorous cleaning regime that is both labor and time intensive. To combat this, a slight nitrogen purge gas is sent down the internal hollow portion of the auxiliary lance and emerges at the connector end of the lance to flush the vapor away from the contacts. Although this purge is an improvement, it does not entirely eliminate the problem. Such an internal hollow portion of the auxiliary lance is part of a gas path within the meaning of the present invention.

This condition and a solution are well described in Japanese patent application publication JP 2000-28438 A. This immersion device is equipped with an electronic circuit which digitizes the DC voltage signals and transmits these first by a single antenna wire and then by radio transmission, thus avoiding but not eliminating the problem of water, tar and resin deposition on the electrical contact members of the lance. The time and expense of cleaning is compared to the additional technical effort of the radio transmitter and as a result has found limited use.

With a sampler as described in U.S. 2014/0318276 A1, it is possible to use an inert gas purge from the lance to the sampling chamber. Reproducible gas pressure is required to obtain these rapid analysis samples, thereby necessitating an electrical and gas contact system that is free of the water, tar and resin condensates that have prevented trouble free operation of the lance measuring system.

A lance having a tubular end portion may comprise O-ring seals on the outer circumference. This tubular end portion comprising the O-ring seals has to be inserted into a detachable tubular connecting element of a coupling piece or of a carrier, in order to provide a gas tight connection between the lance and the coupling piece or the carrier. The lance and the coupling piece thus provide a gas path which may be directed to a sampling chamber.

While immersed, the purge gas flow is then implemented, as anticipated. However, once the coupling piece is disconnected, deposition of the tars and the resin on the O-rings may take place, preventing a gas tight connection between the tubular end portion of the lance and a tube of a further coupling piece.

BRIEF SUMMARY OF THE INVENTION

The object of the invention is to provide an immersion device for molten metal which allows a trouble free operation. The object of the invention is achieved by an immersion device comprising the features described and claimed in the following.

An immersion device for molten metal according to the invention comprises a measuring head, a carrier for the measuring head and a lance which is detachably connected to the carrier or can be connected to the carrier by a detachable tubular connecting element. There is a gas path from the lance to the carrier. The tubular connecting element or the carrier comprises one or more wipers, which wipe the connecting surface of the lance during attachment of the tubular connecting element or the carrier to the lance and/or during detachment of the tubular connecting element from the lance or the carrier.

Thus, replacing the carrier or the carrier together with the connecting element cleans the connecting surface of the lance, which guarantees a gas tight connection between the tubular end portion of the lance and the tubular connecting element and allows a trouble-free operation.

In a preferred embodiment of the invention, the wipers comprise one or more fins which allow a good cleaning effect.

In a preferred embodiment of the invention, the wipers and the tubular connecting element are made of one piece. One advantage is the reduced number of parts.

In a preferred embodiment of the invention, the one or more wipers are pressed against the connecting surface of the lance when the tubular connecting element is connected to the lance, which allows a good cleaning effect. The same is true if there is a direct connection between the carrier and the lance.

In a preferred embodiment of the invention, the wipers protrude from a tubular surface of the tubular connecting element or carrier, which allows a good cleaning effect.

In a preferred embodiment of the invention, the wipers is separated from a tubular surface of the tubular connecting element or carrier by one or more slits, which allows a good cleaning effect due to a more flexible behavior of the wipers.

In a preferred embodiment of the invention, the one or more wipers are ring-shaped, which allows a gas tight connection between a connecting surface of the lance and the detachable tubular connecting element or carrier.

In a preferred embodiment of the invention, the connecting surface of the lance is an inner surface of a tubular end portion of the lance. The connecting surface is thus protected, which prevents a contamination of the connecting surface.

In a preferred embodiment of the invention, the wipers are formed of metal or plastic, which allows a good cleaning effect.

In a preferred embodiment of the invention, the wipers provide the gas tight connection between the connecting surface of the lance and the detachable tubular connecting element or carrier. Further parts, such as O-rings are possible, but not necessary, in order to provide a gas tight connection, which reduces the number of parts.

In a preferred embodiment of the invention, the carrier comprises a cardboard tube.

In a preferred embodiment of the invention, the measuring head comprises a sampler for molten metal or a sensor for detecting a temperature of molten metal, an oxygen content of molten metal, a carbon content of molten metal, or a bath level of molten metal.

In a preferred embodiment of the invention, the lance is formed of metal for stability reasons.

In a preferred embodiment of the invention, the lance and the carrier cover an internal wiring and/or one or more electrical connections.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
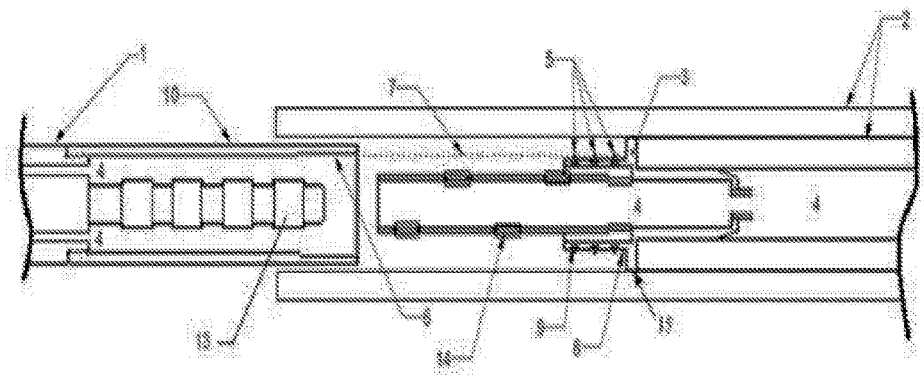
FIG. 1 is a lateral view of longitudinal section of an immersion device according to an embodiment of the invention.
Figure 2:
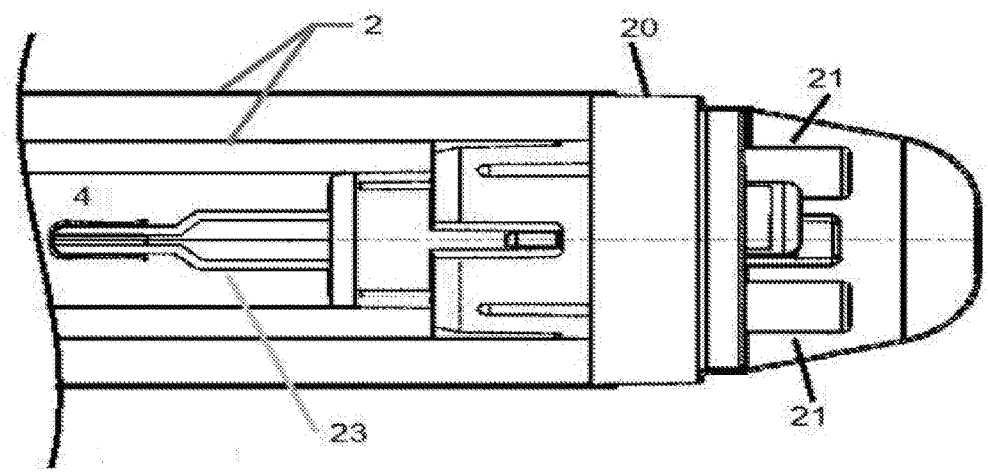
FIG. 2 is a lateral view of a longitudinal section of a measuring head having measuring elements, a sampler, and the carrier tubes for use in an embodiment of the invention.

An immersion device for molten metal according to an embodiment of the invention comprises a carrier for a measuring head 20 comprising measuring elements, such as sensors 21, a molten metal sampling device 23, and a carrier (see FIG. 2). The carrier comprises hollow tubes 2 and a lance in the form of a hollow tube 1 as shown in longitudinal section in FIG. 1. The lance 1 can be connected to the carrier comprising the tubes 2 by a detachable tubular connecting element 3.

The immersion device comprises a gas path 4 provided by the tubular lance 1, the tubular connecting element 3 and the tubular carrier 2, when the tubular lance 1, the tubular connecting element 3 and the tubular carrier 2 are connected together. The gas path supplies purge gas and vacuum for the sampling device 23.

The detachable tubular connecting element comprises wipers in the form of three ring-shaped fins 5 on an outer circumference of the tubular connecting element 3, which wipe the inner connecting surface 6 of the tubular end portion 10 of the lance 1 during insertion of the tubular connecting element 3 into the lance 1 and during detachment of the tubular connecting element 3 from the lance 1.

The fins 5 and the tubular connecting element 3 are made of one piece, in order to avoid the production of a plurality of pieces and a need to attach the fins 5 to the tubular connecting element 3. Further, the one piece production comes with the advantage that the fins 5 are connected to the tubular connecting element 3 in a reliable and gas tight manner.

Since the fins 5 extend beyond the circumference (represented by the broken line 7) of the inner connecting surface 6, the fins 5 are pressed against the connecting surface 6 of the lance 1 when the tubular connecting element 3 is connected to the lance 1. As a consequence, there is a gas tight connection between the fins 5 and the inner connecting surface 6. Since each fin 5 surrounds the tubular connecting element 3 in a circular manner, there is a gas tight connection between the lance 1 and the tubular connecting element 3 when the tubular connecting element 3 has been inserted into the lance 1.

The fins 5 protrude from a tubular outer surface 8 of the tubular connecting element 3 as shown in FIG. 1. The fins 5 are separated from the adjacent tubular outer surface 8 of the tubular connecting element 3 by annular slits 9, so that the fins are more flexible, which allows a good cleaning effect and a reliable gas-tight connection.

The connecting surface 6 of the lance 1 is an inner surface of a tubular end portion 10 of the lance 1.

The hollow tubes 2 of the carrier may be cardboard tubes. The lance 1 can be made of metal, and the tubular connecting element 3 is made of plastic. The lance 1 and the hollow tubes 2 of the carrier cover an internal wiring, not shown, which relays the electrical signals from electrical connectors 13, 14. The electrical connectors 13 of the lance are inserted into and make contact with the electrical connectors 14 of the tubular connecting element 3, when the lance 1 is attached to the hollow tube 2 of the carrier via the tubular connecting element 3.

A ring-shaped stopper 15 for the hollow tube 2 of the carrier and the lance 1 protrudes from the outer surface 8 of the tubular connecting element 3, which facilitates the handling of the connection.

The carrier may comprise hollow shafts formed, for example, of cardboard. A measuring head may be attached to the immersion end of the outer hollow shaft. The outer hollow shaft of the carrier may have a length of 2 m to 3 m, for example a length about 2.5 m. When the lance 1 is connected to the carrier, the outer hollow shaft of the carrier covers part of the lance 1.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An immersion device for molten metal, the device comprising a measuring head (20), a carrier (2) for the measuring head, a lance (1) detachably connected to the carrier (2), and wipers (5) comprising at least one fin which wipe a connecting surface (6) of the lance (1) during attaching and/or detaching the lance (1) to/from the carrier,
   wherein the lance (1) and the carrier (2) cover at least one electrical connector (13, 14),
   wherein the connecting surface (6) of the lance (1) is an inner surface of a tubular end portion (10) of the lance (1)
   wherein the wipers (5) protrude from a tubular surface (8) of a detachable connecting element (3) or from a tubular surface of the carrier (2), and
   wherein there is a gas tight connection between the at least one fin and the connecting surface.

2. The immersion device according to claim 1, wherein the wipers (5) are part of the detachable connecting element (3) which is made in one piece for detachably connecting the lance to the carrier.

3. The immersion device according to claim 1, wherein the wipers are pressed against the connecting surface (6) of the lance (1).

4. The immersion device according to claim 1, wherein the wipers (5) are separated from the tubular surface (8) of the detachable connecting element (3) or from the tubular surface of the carrier (2) by at least one slit (9).

5. The immersion device according to claim 1, wherein the wipers (5) are ring-shaped.

6. The immersion device according to claim 1, wherein the wipers (5) provide a gas tight connection between the connecting surface (6) of the lance (1) and the detachable connecting element (3).

7. The immersion device according to claim 6, wherein the wipers (5) are part of the gas tight connection.

8. The immersion device according to claim 1, wherein the carrier comprises a cardboard tube.

9. The immersion device according to claim 1, wherein the measuring head comprises a sampler (23) for molten metal.

10. The immersion device according to claim 1, wherein the measuring head comprises at least one sensor (21) for detecting at least one of the following: a temperature of the molten metal, an oxygen content of the molten metal, a carbon content of the molten metal, or a bath level of the molten metal.

11. The immersion device according to claim 1, wherein the lance (1) is formed of metal.

12. The immersion device according to claim 1, wherein the lance (1) and the carrier (2) cover an internal wiring.

13. A method for steelmaking comprising using the immersion device according to claim 1 to monitor the molten metal, and replacing the carrier and the measuring head after being used for monitoring the molten metal.

14. The immersion device according to claim 1, further comprising at least one O-ring for providing the gas tight connection between the at least one fin and the connecting surface.

* * * * *